United States Patent [19]

Minamihara et al.

[11] Patent Number: 5,827,720
[45] Date of Patent: Oct. 27, 1998

[54] α-GLUCOSIDASE, AND A PROCESS FOR PRODUCING THE SAME

[75] Inventors: Tomoyuki Minamihara; Kimiharu Okada, both of Saitama; Masaru Suzuki, Chiba, all of Japan

[73] Assignee: Kikkoman Corporation, Chiba, Japan

[21] Appl. No.: 775,459

[22] Filed: Dec. 30, 1996

[30] Foreign Application Priority Data

Dec. 28, 1995 [JP] Japan ................................. 7-352421

[51] Int. Cl.$^6$ .............................. C12P 19/20; C12N 9/26; C12N 1/20
[52] U.S. Cl. ........................... 435/201; 435/96; 435/200; 435/252.5
[58] Field of Search ..................... 435/200, 201, 435/96, 252.5

[56] References Cited

FOREIGN PATENT DOCUMENTS 6-34715  5/1994  Japan .

OTHER PUBLICATIONS

Mikio Yamamoto et al., Purification and Properties of an Oligo–1,6–D–Glucosidase From an Alkalophilic Bacillus Species. Carbohydrate Research, 197, (1990) 227–235.

Yuzuru Suzuki et al., Assignment of ap–Nitrophenyl α–D–Glucopyranosidase of Bacillus Stearothermophilus ATCC 12016 to a Novel Exo–α–1,4–Glucosidase Active for Oligomaltosaccharides and α–Glucans, Biochimica et Biophysica Acta, 787, (1984)281–289.

Yuji Oda et al., Purification and Characterization of α–Glucosidase from Torulaspora pretoriensis YK–1, Biosci. Biotech. Biochem., 57(11), 1902–1905, 1993.

*Primary Examiner*—Herbert J. Lilling
*Attorney, Agent, or Firm*—Finnegan, Henderson, Farabow, Garrett & Dunner, L.L.P.

[57] ABSTRACT

The present invention relates to novel α-glucosidase being excellent in stability to heat and pH, and hydrolyzing α-glucoside linkages to form α-D-glucose, acting on maltose, maltotriose, maltotetraose, PNPG, PNPG2, isomaltose and sucrose, but hardly acting on maltooligosaccharides with a degree of polymerization of maltopentaoside or more, and completely not acting on soluble starch, as well as to a process for producing the same by use of a strain belonging to the genus Bacillus capable of producing α-glucosidase. α-Glucosidase which is useful as a coupling enzyme for quantification such as measurement of α-amylase activity, or in formation of monosaccharides such as glucose and fructose etc., from oligosaccharides, and enzymatic synthesis of heterooligosaccharides, can be produced easily and inexpensively.

3 Claims, 3 Drawing Sheets

α-GLUCOSIDASE, AND A PROCESS FOR PRODUCING THE SAME

FILED OF THE INVENTION

The present invention relates to novel α-glucosidase useful as a coupling enzyme in measuring α-amylase activity or quantifying chlorine ions, or quantifying maltooligosaccharides and as an enzyme for deletion thereof, which acts on maltose, maltotriose, maltotetraose, paranitrophenyl-α-D-glucopyranoside (referred to hereinafter as "PNPG"), paranitrophenyl-α-D-maltoside (referred to hereinafter as "PNPG2"), isomaltose, and sucrose to hydrolyze their α-glucoside linkages to form α-D-glucose, but hardly acts on maltooligosaccharides with a degree of polymerization of maltopentaoside or more, and does completely not act on soluble starch and which is excellent in thermostability, pH resistance etc., as well as to a process for producing the same.

BACKGROUND OF THE INVENTION

The enzyme hydrolyzing an α-1,4-glucoside linkage to form α-D-glucose is present widely in the biological world, and includes e.g. α-glucosidase present in yeast, filamentous fungi, bacteria, mammals, plant seeds etc., and oligo-1,6-D-glucosidase derived from the genus Bacillus as described in e.g. Carbohydrate Research, Vol. 197, p.p. 227 to 235 (1990).

Conventionally known α-glucosidase acting well on maltose and PNPG includes those derived from yeast as described in Biosci. Biotech. Biochem. Vol. 57, No. 11, pp. 1902 to 1905 (1993) and from *Bacillus stearothermophilus* as described in Biochimica et Biophysica Acta, Vol. 787, pp. 281 to 289 (1984). Commercial products of such enzyme include those derived from yeast (Sigma, Toyoboseki K. K.) and from microorganisms (Toyoboseki K. K.).

In the above-described α-glucosidase, however, the yeast-derived α-glucosidase lacks stability to heat, pH, inhibitor etc. and is problematic in production of the enzyme and for use at ordinary temperature. The enzyme derived from *Bacillus stearothermophilus* and the commercial enzymes derived from microorganisms are superior in thermostability, but lack stability to inhibitors such as sodium dodecyl sulfate (SDS), p-chloromercuribenzoic acid (PCMB) etc.. In respect of substrate specificity, these enzymes do not act on α-1,6-glucoside linkages, so they can not use the reaction. Moreover these enzymes act on soluble starch and maltooligosaccharides with a degree of polymerization of maltopentaose or more, so they are not suitable in hydrolysis of said linkages or as coupling enzymes for use in measurement of α-amylase activity with such compounds as substrate.

SUMMARY OF THE INVENTION

The present invention was made to overcome the problems of the above conventional α-glucosidase, and the object of the present invention is to provide α-glucosidase which can be used as a coupling enzyme capable of acting on maltooligosaccharides with a degree of maltotetraose or less and PNPG, PNPG 2 etc. and used in measuring α-amylase activity or quantifying chlorine ions, or quantifying maltooligosaccharides such as maltose and as an enzyme for deletion thereof, or in industrial production of monosaccharides such as glucose and fructose etc., from oligosaccharides, as well as a process for producing said enzyme inexpensively and easily.

The present inventors searched for a microorganism capable of producing α-glucosidase in the natural world. As a result, they found that one strain of the genus Bacillus separated from soil produces novel α-glucosidase excellent in stability which acts on maltose, maltotriose, maltotetraose, PNPG, PNPG2, but not on soluble starch. On the basis of this finding, they arrived at the completion of the present invention.

That is, the present invention is novel α-glucosidase with the following physicochemical properties:

(a) action: hydrolyzing an α-glucoside linkage to form α-D-glucose;

(b) substrate specificity: acting on maltose, maltotriose, maltotetraose, paranitrophenyl-α-D-glucopyranoside, paranitrophenyl-α-D-maltoside, isomaltose, and sucrose, but hardly acting on maltooligosaccharides with a degree of polymerization of maltopentaoside or more, and completely not acting on soluble starch;

(c) optimum pH and stable pH range: optimum pH in about pH 6.0 to 9.0, and stable pH range from pH 5.0 to 10.0 at 25° C. for 20 hours in the presence of 0.2 % bovine serum albumin;

(d) suitable temperature range for action: from about 52° C. to about 55° C.;

(e) conditions for inactivation by pH and temperature: stable in the range of pH 5.0 to 10.0, and completely inactivated at pH 4.5 or less or pH 11.0 or more, for 20 hours at 25° C. in the presence of 0.2% bovine serum albumin, and stable at a temperature of up to 50° C. at pH 7.0 for 15 minutes, and completely inactivated at a temperature of 60° C. or more; and (f) molecular weight: about 61,300±5,000 (gel filtration). Further, the present invention is a process for producing said α-glucosidase, which comprises culturing a strain belonging to the genus Bacillus capable of producing α-glucosidase in a culture and then recovering the α-glucosidase from the culture.

PREFERRED EMBODIMENTS OF THE PRESENT INVENTION

Figure 1:
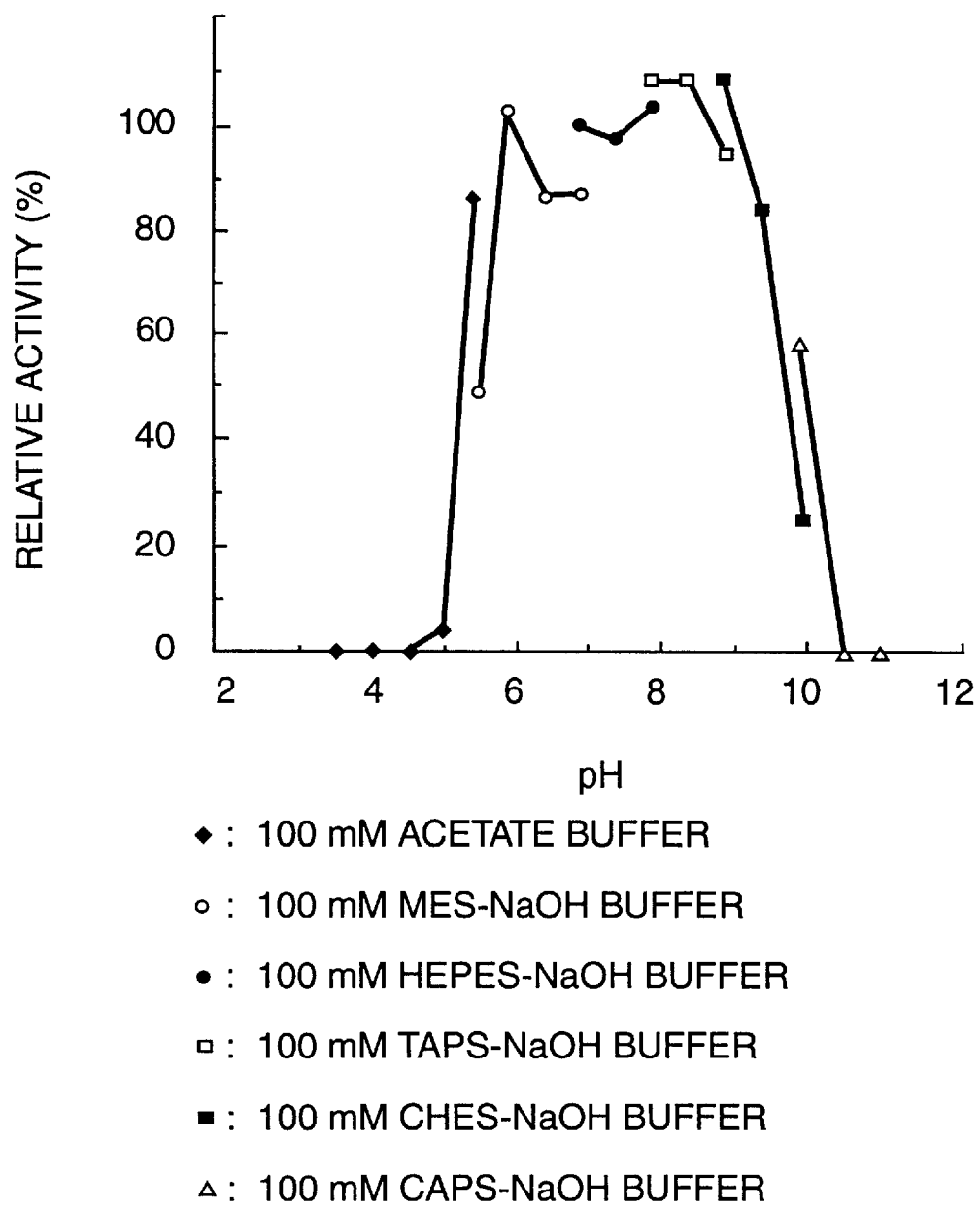
FIG. 1 is a graph showing the optimum pH of the present enzyme at 37° C.

The physicochemical properties of the novel α-glucosidase of the present invention (referred to hereinafter as the present enzyme) are as follows:

(1) Action:

The present enzyme hydrolyzes α-glucoside-linkage-containings glycosides or oligosaccharides to cleave them from the nonreducing terminal side to form α-D-glucose.

(2) Substrate specificity:

The present enzyme acts on maltose, maltotriose, maltotetraose, PNPG, PNPG2, isomaltose and sucrose, but hardly acts on maltooligosaccharides with a degree of polymerization of maltopentaoside or more, and does completely not act on soluble starch, amylopectin and amylose.

The relative activity of the present enzyme to various kinds of substrate is shown in Table 1.

TABLE 1

Substrate Specificity

| Substrate | Produced Glucose (%) |
|---|---|
| *maltose | 10.2 |
| maltotriose | 112.9 |
| maltotetraose | 13.9 |
| maltopentaose | 1.4 |
| maltohexaose | 0.15 |
| maltoheptaose | 0.15 |
| maltooctaose | 0 |
| *isomaltose | 66.1 |
| sucrose | 29.7 |
| **soluble starch | 0 |
| **amylopectin | 0 |
| **amylose | 0 |
| PNPG | 100 |
| PNPG2 | 9.4 |

*Half of produced glucose is shown.
**The final concentration of substrate was 1%.

The conditions and method for measuring the relative activity are as follows:

0.11 ml of each substrate (20 mM), 0.49 ml of 100 mM potassium phosphate buffer (pH 7.0) containing 0.1% bovine serum albumin (BSA) and 0.39 ml of distilled water were mixed and pre-incubated at 37° C. for 5 minutes. Thereafter, 0.01 ml of 0.303 mg/ml of the present enzyme in 100 mM potassium phosphate buffer (pH 7.0) containing 0.1% BSA was added to the reaction solution, followed by hydrolysis reaction accurately at 37° C. for 15 minutes. Then, the test tube containing the reaction solution was placed in boiling water to stop the enzyme reaction. The amount of glucose thus formed was determined using Glucose C II Test Wako (Wako Pure Chemical Industries, Ltd.) in the glucose-oxidase method and indicated as relative activity to the amount (as 100%) of glucose formed from PNPG.

(3) Optimum pH and stable pH range:

To determine the optimum pH of the present enzyme, the following buffers were used: 100 mM acetate-sodium acetate buffer (pH 3.5 to 5.5), 100 mM MES-NaOH buffer (pH 5.5 to 7.0), 100 mM HEPES-NaOH buffer (pH 7.0 to 8.0), 100 mM TAPS-NaOH buffer (pH 8.0 to 9.0), 100 mM CHES-NaOH buffer (pH 9.0 to 10.0), and 100 mM CAPS-NaOH buffer (pH 10.0 to 11.0). For measurement of activity, 0.7 ml of each buffer and 0.25 ml of 20 mM PNPG were put to a test tube and pre-incubated at 37° C. for 5 minutes, and then 0.05 ml of 0.00327 mg/ml of the present enzyme in 10 mM potassium phosphate buffer (pH 7.0) containing 0.2 % BSA was added to it, followed by reaction accurately at 37° C. for 15 minutes. Then, 1 ml of 0.2 M sodium carbonate was added to the reaction solution to stop the reaction. The paranitrophenol thus formed was colored and measured for absorbance at 400 nm in a Hitachi spectrophotometer (U-2000A, manufactured by Hitachi Ltd.) to determine its amount.

As shown in FIG. 1, the result indicated that the optimum pH of the present enzyme ranged from pH 6.0 to 9.0.

To determine the stable pH range of the present enzyme, the following buffers were used: 100 mM acetate-sodium acetate buffer (pH 3.5 to 5.5), 100 mM MES-NaOH buffer (pH 5.5 to 7.0), 100 mM HEPES-NaOH buffer (pH 7.0 to 8.0), 100 mM TAPS-NaOH buffer (pH 8.0 to 9.0), 100 mM CHES-NaOH buffer (pH 9.0 to 10.0) and 100 mM CAPS-NaOH buffer (pH 10.0 to 11.0), 100 mM potassium phosphate buffer (pH 6.5 to 8.0), and 100 mM Tris-HCl buffer (pH 7.5 to 9.0).

Figure 2:
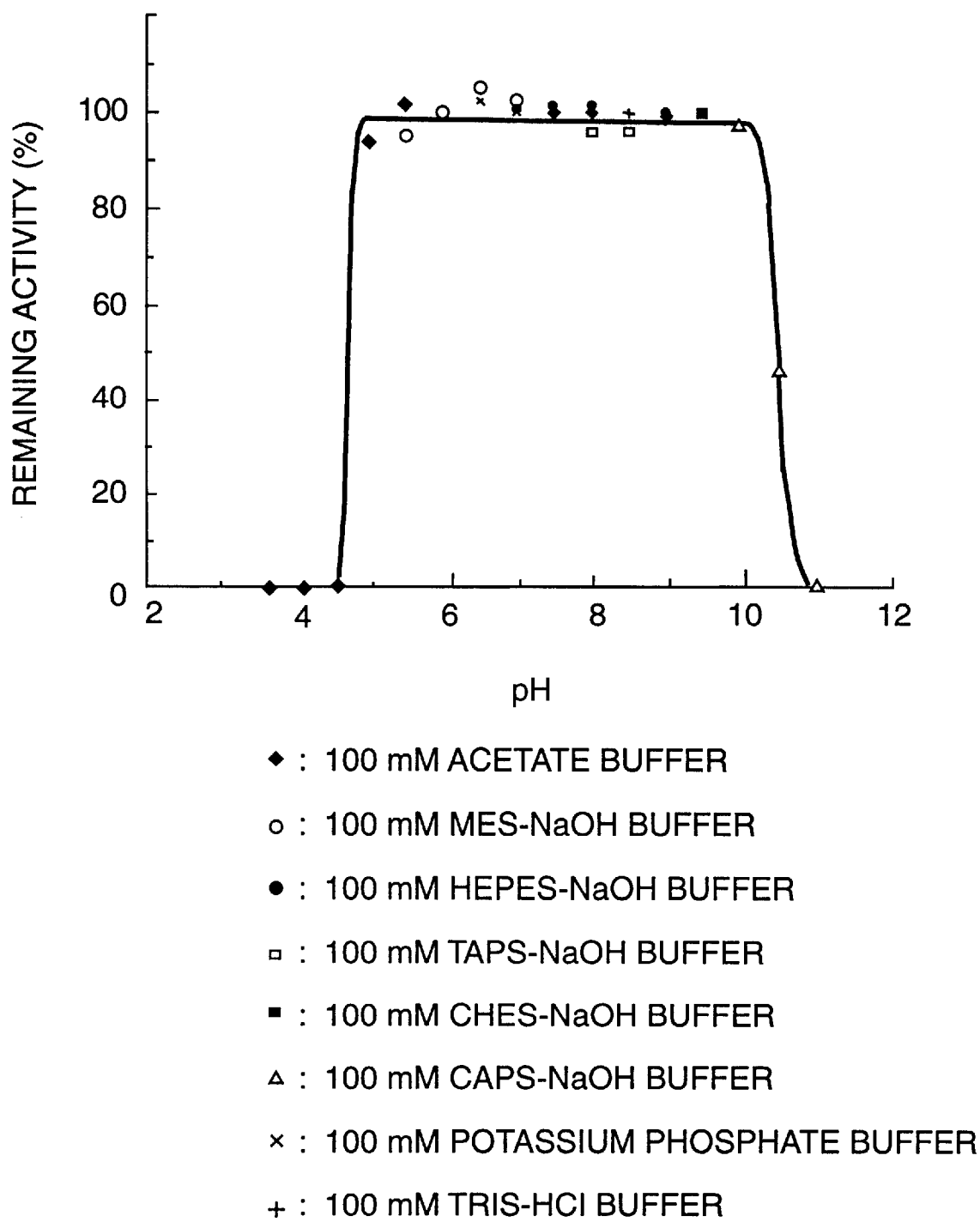
FIG. 2 is a graph showing the stable pH range of the present enzyme for 20 hours at 25° C. in the presence of 0.2% bovine serum albumin (BSA).

0.01 ml of 0.34 mg/ml of the present enzyme and 0.04 ml of 0.5% BSA were added to 0.05 ml of each buffer and reacted at 25° C. for 20 hours. After the reaction, the reaction solution was diluted 100-fold with 100 mM potassium phosphate buffer pH 7.0 containing 0.2% BSA and left for 10 minutes. The remaining enzyme activity in each sample was determined in a usual manner. As shown in FIG. 2, the result indicated that the stable pH range of the present enzyme is pH 5.0 to 10.0.

(4) Suitable temperature range for action:

The substrate and enzyme mixture described in titer measurement below were used for determination of the titer of the present enzyme at various temperatures.

Figure 3:
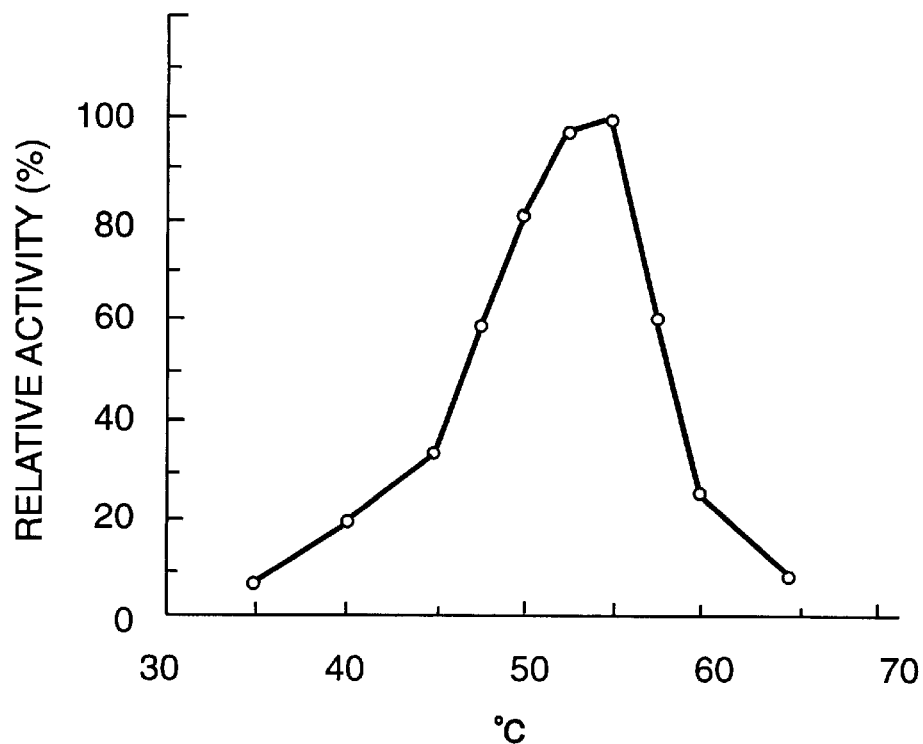
FIG. 3 is a graph showing the suitable temperature range for the action of the present enzyme at pH 7.0.

As shown in FIG. 3, the result indicated that the optimum temperature of the present enzyme ranges from about 52° C. to about 55° C.

(5) Conditions for inactivation by pH and temperature:

The present enzyme is stable in the range of pH 5.0 to 10.0 at 25° C. for 20 hours in the presence of 0.2% BSA, and as can be seen from FIG. 2, it was completely inactivated at pH 4.5 or less or at pH 11.0 or more.

Figure 4:
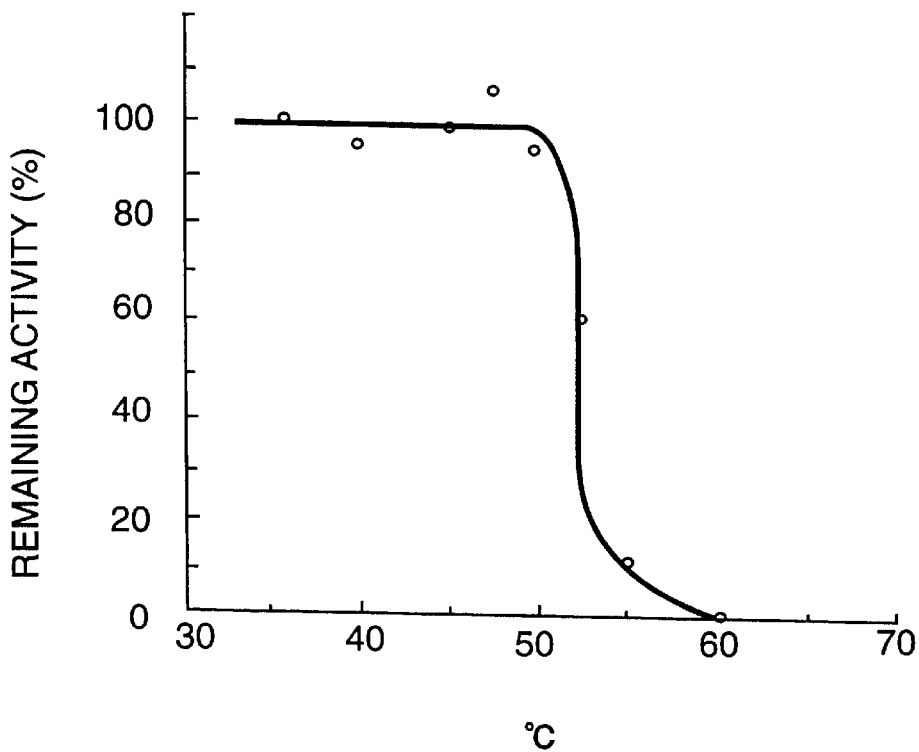
FIG. 4 is a graph showing the thermostability of the present enzyme at pH 7.0.

For thermostability, 0.0606 mg/ml of the present enzyme in 100 mM potassium phosphate buffer, pH 7.0 was incubated at predetermined temperatures for 15 minutes. After incubation, the reaction solution was diluted 100-fold with 10 mM potassium phosphate buffer pH 7.0 containing 0.2% BSA, and the remaining enzyme activity was determined in a usual manner. As shown in FIG. 4, the result indicated that the present enzyme is stable at a temperature of up to 50° C. under the above conditions and it is completely inactivated at a temperature of 60° C. or more for 15 minutes at pH 7.0.

(6) Molecular weight:

Gel filtration by TSK gel G3000 SWXL (Tosoh Corporation) indicated that the molecular weight is about 61,300±5,000. SDS-polyacrylamide gel electrophoresis (SDS-PAGE) (gel: Multigel 10–20, a 10–20% amide gradient gel, produced by Dai-Ichi Kagaku) showed a single band, indicating that it was purified sufficiently and that the molecular weight was 60,200. From this result and in consideration of the molecular weight by gel filtration, it was estimated that the present enzyme has a monomer structure.

(7) Titer measurement:

The measurement of the titer of the present enzyme was carried out in the following manner. The amount of the enzyme causing 1 μ mol paranitrophenol per minute to be released from PNPG was assumed as 1 U of the enzyme. (Preparation of a substrate solution, a buffer, a reaction terminating solution, and an enzyme diluent)

Substrate solution (Solution 1):

20 mM PNPG, prepared by dissolving 0.603 g PNPG in distilled water to give 100 ml solution.

Buffer (Solution 2):

0.1 M potassium phosphate buffer, pH 7.0, prepared by mixing 0.1 M potassium dihydrogen phosphate with 0.1 M dipotassium hydrogen phosphate and adjusting the mixture to pH 7.0.

Reaction terminating solution (Solution 3):

0.2 M sodium carbonate, prepared by dissolving 21.2 g anhydrous sodium carbonate in distilled water to give 1000 ml solution.

Enzyme diluent:

0.01 M potassium phosphate buffer, pH 7.0 containing 0.2% BSA.

(Procedures for measurement)

First, 0.25 ml of Solution 1 and 0.5 ml of Solution 2 were mixed and pre-incubated at 37° C. for 5 minutes, and then the solution was mixed with 0.25 ml enzyme solution (about 0.005 to 0.03 U/ml) and reacted accurately for 15 minutes at 37° C.

Then, the reaction was stopped by adding 1 ml of Solution 3 to the reaction solution and the paranitrophenol thus formed was colored. This sample was measured for absorbance at 400 nm in a spectrophotometer (U-2000A, Hitachi Ltd.).

As the blank, the substrate solution and the buffer were mixed and pre-incubated, and then the solution was incubated accurately for 15 minutes in the absence of the enzyme solution, followed by adding 1 ml of Solution 3 to it to stop the reaction. Then, the enzyme solution was added to the reaction solution and the blank absorbance was determined.

(Calculation of titer)

From the sample absorbance and blank absorbance thus determined, titer was determined according to the following formula:

$$U/ml = \frac{(\text{sample absorbance} - \text{blank absorbance}) \times 2(ml) \times \text{degree of dilution}}{18.1(cm^2/\mu\,mol) \times 1(cm) \times 15(min) \times 0.25(ml)}$$

(8) Stability to inhibitors:

The effect of treatment with various inhibitors was evaluated in the following manner.

0.1 ml of 0.0667 mg/ml of the present enzyme in 100 mM HEPES-NaOH buffer, pH 7.0 containing 0.2% BSA was added to 0.01 ml of 22 mM inhibitor (1.1% in the case of a surfactant as inhibitor) and incubated at 25° C. for 1 hour. Then, the sample was diluted 100-fold with 10 mM potassium phosphate buffer (pH 7.0) containing 0.2% BSA, and the remaining activity was determined in the same manner as above in titer measurement.

As shown in Table 2, the result indicated that the present enzyme is inactivated with heavy metals i.e. lead, copper, mercury and silver, but not affected by SDS, PCMB or N-ethylmaleimide.

TABLE 2

Effect of Treatment with Inhibitor

| inhibitor | remaining activity (%) | inhibitor | remaining activity (%) |
|---|---|---|---|
| control | 100 | *Tween 20 | 100.8 |
| $CoCl_2$ | 99.8 | *Triton X-100 | 105.8 |
| $NiSO_4$ | 98.7 | *Tween 80 | 107.7 |
| $PbAc_2$ | 46.0 | *SDS | 104.2 |
| $ZnSO_4$ | 89.2 | N-ethylmaleimide | 107.5 |
| $MnSO_4$ | 97.3 | sodium azide | 105.0 |

TABLE 2-continued

Effect of Treatment with Inhibitor

| inhibitor | remaining activity (%) | inhibitor | remaining activity (%) |
|---|---|---|---|
| $FeCl_2$ | 96.7 | 2-mercaptoethanol | 99.6 |
| $CuSO_4$ | 30.2 | glutathione | 102.5 |
| $MgCl_2$ | 104.8 | dithiothreitol | 105.4 |
| $BaCl_2$ | 112.7 | o-phenanthroline | 99.4 |
| $CaCl_2$ | 113.1 | PCMB | 97.7 |
| $HgCl_2$ | 8.1 | monoiodoacetic acid | 98.5 |
| $AgNO_3$ | 5.0 | 2-nitrobenzoic acid | 102.7 |
| | | EDTA-2Na | 106.4 |

*0.1% inhibitor was used.

(9) (Km value):

The Km value as determined by Lineweaver-Burk plotting is $5.5 \times 10^{-5}$ M at pH 7.0, 37° C. with PNPG as substrate, and the affinity of the present enzyme for synthetic substrate is extremely high.

(10) Purification method:

The isolation and purification of the present enzyme can be effected in conventional procedures, for example by salting-out with ammonium sulfate, precipitation with organic solvent, ion-exchange chromatography, gel filtration chromatography, absorption chromatography, affinity chromatography, electrophoresis, hydrophobic chromatography, and these may be used singly or in suitable combination.

The present enzyme with the above-described physicochemical properties is novel for the following reason.

α-Glucosidase derived from various microorganisms were found as described above. To compare the present enzyme with such known enzyme derived from yeast and *Bacillus stearothermophilus*, their principal physicochemical properties are shown in Table 3.

In Table 3, the data on yeast-derived α-glucosidase in (Note 1) are quoted from Biosci. Biotech. Biochem., Vol. 57, No. 11, pp. 1902 to 1905 (1993) and the data on *Bacillus stearothermophilus*—derived α-glucosidase in (Note 2) from Biochimica et Biophysica Acta, Vol. 787, pp. 281 to 289 (1984).

TABLE 3

Comparison between the present enzyme and known enzyme

| | present enzyme | known enzyme from yeast (Note 1) | known enzyme from *Bacillus stearothermophilus* (Note 2) |
|---|---|---|---|
| molecular weight | 61,300 ± 5,000 (gel filtration) | 60,000 (gel filtration) | 47,000 (gel filtration) |
| substrate specificity (substrate to be acted on) | maltose, maltotriose, PNPG, PNPG2, isomaltose, sucrose etc. | maltose, maltotriose, PNPG, isomaltose, sucrose | maltooligosaccharides ranging from maltose to maltohexaose, PNPG, soluble starch amylose, amylopectin isomaltose |
| substrate specificity (substrate to be hardly or not acted on) | maltooligosaccharides not less than maltopentaose, and soluble starch | soluble starch | |
| optimum pH | 6.0 to 9.0 (reaction at 37° C.) | 6.8 (reaction at 30° C.) | 6.4 (reaction at 37° C.) |
| stable pH range | 5.0 to 10.0 (treatment at 25° C., 20 hours in the presence of 0.2% BSA) | 5.0 to 8.0 (treatment at 4° C., 16 hours) | 7.4 to 10.6 (treatment at 37° C., 15 hours) |
| optimum temperature | 52 to 55° C. (pH 7.0) | 35° C. (pH 6.8) | 70° C. (pH 6.8) |
| thermostability | 50° C. (treatment at pH 7.0, 15 min.) | 30° C. (treatment at pH 6.8, 10 min.) | 65° C. (treatment at pH 6.8, 15 min.) |

As can be seen from Table 3, the present enzyme hardly acts on maltooligosaccharides of maltopentaose or more and does completely not act on amylose, amylopectin or soluble starch in substrate specificity and thus differs from the enzyme derived from *Bacillus stearothermophilus*. In addition, the present enzyme is useful as e.g. a coupling enzyme for measurement of amylase activity using soluble starch at about neutral pH.

Further, the present enzyme differs from the yeast-derived enzyme in being superior in stable pH range and thermostability although the tendency of substrate specificity is similar.

Accordingly, the present enzyme is stable at the conventionally used temperature range of about 25° to 45° C. and the enzyme purification is feasible at the broad range of pH 5.0 to 10.0, to facilitate purification for producing the present enzyme.

From the foregoing, the present enzyme is novel α-glucosidase having useful properties absent in the conventional α-glucosidase.

The process for producing the present enzyme is described below.

The microorganism used may be any microorganisms belonging to the genus Bacillus capable of producing the present enzyme or variants or mutants of such microorganisms. One example of such microorganisms is Bacillus sp. KS-108a, and its variant or mutant can also be used. Bacillus sp. KS-108a is a strain which was isolated from the soil in Kumamoto Prefecture by the present inventors. The microbial properties are shown below.

The experiment for identification of the microbial properties was conducted on the basis of "Biseibutsu no Bunrui to Doutei" (Classification and Identification of Microorganisms) compiled by Takeji Hasegawa and published in 1975 by Tokyo University tress. For its classification and identification, Berjey's Manual of Determinative Bacteriology, 8th ed. (1974) was consulted.

Microbial properties of Bacillus sp. KS-108a:
(A) Morphological properties
  Observation under a microscope (cultured at 50° C. for 5 to 7 hours in a meat agar medium, pH 7.0).
  (1) Cell shape and size: rod, 0.1–0.5×1–7 microns in size.
  (2) Motility: yes.
  (3) Spore formation: yes.
  (4) Gram stainablity: positive.
(B) Growth states in each medium (pH 7.0)
  (1) Broth agar plate culture
    Pale brown round colonies are formed in 16-hour stationary culture at 50° C. No production of pigments.
  (2) Broth agar slant culture
    Grown in 16-hour culture at 50° C.
  (3) Broth liquid culture
    The culture becomes slightly turbid (i.e. indicating growth) in 16-hour stationary culture at 50° C. A thick microbial film occurs.
  (4) Broth gelatin culture
    The gelatin is not liquefied in 3-day stationary culture at 50° C.
  (5) Litmus milk culture
    In 48-hour stationary culture at 50° C., the litmus milk is not solidified or liquefied, neither is acid or alkali formed.
(C) Physiological properties
  The following items were examined mostly in a medium adjusted to pH 7.0.

(1) Reduction of nitrates: yes.
  (2) Denitrification: no.
  (3) MR test: negative.
  (4) VP test: very weakly positive.
  (5) Formation of indole: no.
  (6) Formation of hydrogen sulfide: no.
  (7) Hydrolysis of starch: no.
  (8) Utilization of citric acid: yes.
  (9) Utilization of inorganic nitrogen sources: both nitrate and ammonium salt are utilized.
  (10) Formation of pigments: no.
  (11) Urease: positive.
  (12) Oxidase: weakly positive.
  (13) Catalase: positive.
  (14) Growth range: temperature, 33° to 55° C.; pH, 6.1 to 9.4.
  (15) Attitude toward oxygen: aerobic.
  (16) O-F test (Hugh-Leifson method): oxidation (0.5% glucose was added as carbon source).
  (17) The formation of acids and gases from saccharides: as shown in Table 4, acids are formed from D-glucose, D-fructose, D-mannose, D-xylose, D-arabinose, sucrose, maltose, and D-mannitol, but no gas is formed.

TABLE 4

| Formation of Acid and Gas from Saccharide | | |
|---|---|---|
| saccharide | acid formation | gas formation |
| D-glucose | + | − |
| D-fructose | + | − |
| D-galactose | − | − |
| D-mannose | + | − |
| D-xylose | + | − |
| L-arabinose | + | − |
| sucrose | + | − |
| maltose | + | − |
| raffinose | − | − |
| D-mannitol | + | − |
| D-sorbitol | − | − |
| glycerin | − | − |
| dextrin | − | − |
| starch | − | − |
| inulin | − | − |

Because the present strain having the above microbial properties and the ability to produce novel α-glucosidase is Gram-positive, mobile, and capable of forming spores, it was identified as belonging to the genus Bacillus. Accordingly, the present strain was designated Bacillus sp. KS-108a. The present strain has been deposited as FERM BP-5337 with the National Institute of Bioscience and Human-Technology, Agency of Industrial Science and Technology, Japan.

Any α-glucosidase having the above principal physicochemical properties in respect of action, substrate specificity etc., falls under the scope of the present enzyme, even if there are slight differences in other physicochemical properties. The above-described microorganism is not limiting, and any strain belonging to the genus Bacillus capable of producing said α-glucosidase can be used in the present invention.

For production of the present enzyme by use of the strain belonging to the genus Bacillus capable of producing said α-glucosidase, both synthetic and natural media can be used insofar as they contain a carbon source, nitrogen source, inorganic matter and other nutrients in suitable amounts.

The carbon source may be any carbon compound by which the present enzyme can be induced, and a medium containing e.g. corn syrup powder is preferable. The nitrogen source may be any available nitrogen compounds, and for examples yeast extract, peptone, meant extract, corn starch liquor, soybean powder, amino acids, ammonium sulfate, ammonium nitrate etc. are used.

In addition, salts such as common salt, potassium chloride, magnesium sulfate, manganese chloride, ferrous sulfate, dipotassium hydrogen phosphate, potassium dihydrogen phosphate and sodium carbonate, vitamins, and an antifoaming agent are used. These nutrient sources can be used singly or in combination.

To produce the present enzyme in a liquid medium thus prepared, the microorganism is preferably cultured aerobically in submerged aeration culture with stirring or in shake culture. The initial pH of the medium is adjusted in the range of about pH 6.5 to 7.0, and the microorganism is cultured for at least 7 hours at a temperature of 35° to 55° C., preferably about 50° C. After culture, conventional means can be used for collection of the present enzyme from the culture.

Because the present enzyme is present in the microorganism, it is preferable to separate the microorganism from the culture by e.g. filtration or centrifugation prior to the separation of α-glucosidase from the microorganism. In this case, the microorganism can be used as such or disrupted using means such as ultrasonication, French press, dynamill, or by treatment with lytic enzyme such as lysozyme for cell wall lysis or with a surfactant such as Triton X-100 for enzyme extraction from the microorganism, and these means can be used singly or in suitable combination. Subsequently, insolubles are removed by filtration or centrifugation whereby the present enzyme is obtained in crude form as the supernatant.

To purify the present enzyme from this crude enzyme solution, the conventional means as described can be used.

The present enzyme thus obtained can be used as a coupling enzyme in measuring α-amylase activity or quantifying chlorine ions, or measuring maltooligosaccharides such as maltose or as a deletion enzyme thereof, or as an enzyme for industrial production of monosaccharides such as glucose and fructose etc. from oligosaccharides.

EFFECT OF THE INVENTION

Particularly in respect of substrate specificity, the present enzyme acts on maltose, maltotriose, maltotetraose, paranitrophenyl-α-D-glucopyranoside, paranitrophenyl-α-D-maltoside, isomaltose, and sucrose, but hardly acts on maltooligosaccharides with a degree of polymerization of maltopentaoside or more, and does completely not act on soluble starch and further it is excellent in thermostability, stable in a wide pH range and excellent in stability to a surfactant etc., so that it is extremely useful as a coupling enzyme capable of acting on maltooligosaccharides with a degree of polymerization of maltotetraose or less and PNPG, PNPG2 etc. and used in measuring α-amylase activity or quantifying chlorine ions, or quantifying maltooligosaccharides such as maltose and as an enzyme for deletion thereof, as a substitute for the conventional enzyme derived from yeast.

Further, the present enzyme can also be used in industrial production of monosaccharides such as glucose and fructose etc., from oligosaccharides, as well as in industrial production of rare heterooligosaccharides by its glycosyltransferring action in enzymatic synthesis.

Further, the present enzyme can be obtained in a large amount for a short period of time by culturing the microorganism in the process of the present invention where the present enzyme can be produced easily and inexpensively because by virtue of its stability to heating and pH, the present enzyme can be treated at a temperature of up to 50° C. and purified in the wide range of pH 5 to 10. Hence, the present invention is industrially extremely useful.

EXAMPLES

Hereinafter, the present invention is described in more detail by reference to Examples, which however are not intended to limit the scope of the present invention.
(Example)

100 ml medium (pH 7.0) consisting of 2.0% corn syrup powder (Showa Sangyo K. K.), 2.0% polypeptone, 1.0% yeast extract, 0.01% potassium dihydrogen phosphate, 0.01% dipotassium hydrogen phosphate, 0.01 % magnesium sulfate ·7$H_2O$ and tap water was introduced into a flask and sterilized at 121° C. for 7 minutes. Bacillus sp. KS-108a (FERM BP-5337) was inoculated into this medium and cultured at 40° C. for about 16 hours with shaking in an incubator. The culture in the flask, 100 ml, was transferred to 30-L jar fermenter containing 20 L of the same medium with 2 ml antifoaming agent (Nissan Disfoam CC-485), previously sterilized at 121° C. for 7 minute, and cultured at 50° C. for about 7 hours with stirring at 300 r.p.m. under an inside pressure of 0.5 L with aeration at a rate of 20 L/min. After culture was finished, the microorganism was collected from 20 L culture through Microza PW-303 (Asahi Chemical Industry Co., Ltd.) and washed with tap water, and the bacterial suspension was concentrated to about 10 L.

The purification of the present enzyme was carried out in the following manner.
Step 1 (Preparation of the crude enzyme solution):

1 L of 0.55 M EDTA-2Na (pH 8.0) was added to, and mixed with, the above concentrate of the microorganism, and the microorganism was lyzed at 20° C. for 2 days, followed by adding 200 ml of 5% aqueous protamine (pH 8.0) dropwise to it to remove nucleic acids. The supernatant was introduced into an ultrafiltration membrane and dialyzed against 0.01 M potassium phosphate buffer (pH 7.0) (referred to hereinafter as "buffer A") containing 0.1 M potassium chloride.
Step 2 (Treatment with DEAE-cellulose):

DEAE-cellulose (wet weight: about 9 kg) was added to and mixed with the above dialyzate (about 10 L) to absorb the present enzyme onto it. This resin was then washed with buffer A containing 0. 1 M potassium chloride, and the present enzyme was eluted with buffer A containing 0.3 M potassium chloride. This eluate was concentrated with a hollow-fiber-type ultrafiltration unit and then the buffer in the concentrate was replaced by buffer A containing 0.1 M potassium chloride by dialyzing it against this buffer.
Step 3 (Batchwise treatment with QAE-Sephadex A-50):

1000 ml QAE-Sephadex A-50 was added to and mixed with the above dialyzate (1000 ml) to absorb the present enzyme onto it. This resin was then washed with buffer A containing 0.15 M potassium chloride, and the present enzyme was eluted with buffer A containing 0.2 M potassium chloride. This eluate was concentrated with a hollow-fiber-type ultrafiltration unit and then the buffer in the concentrate was replaced by buffer A containing 0.08 M potassium chloride by dialyzing it against this buffer.
Step 4 (DEAE-Toyopearl 650C column chromatography):

The above dialyzate (500 ml) was applied to a column of DEAE-Toyopearl 650C (4.2×30 cm) to be absorbed onto it. The column was then washed with buffer A containing 0.08 M potassium chloride, and the protein was eluted with a linear gradient of from 0.08 to 0.2 M potassium chloride in buffer A.

The eluted active fraction was concentrated by a hollow-fiber-type ultrafiltration unit, and then the buffer in the concentrate was replaced by buffer A by dialyzing it against this buffer.

Step 5 (Butyl-Toyopearl 650C column chromatography):

200 ml of buffer A containing 2 M ammonium sulfate was added to the above dialyzate (200 ml), and then this sample was applied to a column of Butyl-Toyopearl 650C (4.2×30 cm) to be absorbed onto it. The column was then washed with buffer A containing 1 M ammonium sulfate, and the protein was eluted with a linear gradient of from 1 to 0.7 M ammonium sulfate in buffer A.

The eluted active fraction was concentrated by hollow-fiber-type and membrane-type ultrafiltration units, and then the buffer in the concentrate was replaced by buffer A containing 0.1 potassium chloride by dialyzing it against this buffer.

Step 6 (Gel filtration (Bio-Gel A1. 5 m 200–400 mesh)):

The above dialyzate (about 2 ml) was applied to and passed through a column (2.5×95 cm) packed with Bio-Gel A1. 5 m 200–400 mesh, with buffer A containing 0.1 M potassium chloride as the eluent. The eluted active fraction was collected. By the above purification procedures, a purified enzyme preparation (about 1,061 U, 33.1 U/mg protein) was obtained.

What is claimed is:

1. An isolated α-Glucosidase having physicochemical properties comprising:

(a) action: hydrolyzing an α-glucoside linkage to form α-D-glucose;

(b) substrate specificity: acting on maltose, maltotriose, maltotetraose, paranitrophenyl-α-D-glucopyranoside, paranitrophenyl-α-D-maltoside, isomaltose, and sucrose, but hardly acting on maltooligosaccharides with a degree of polymerization of maltopentaoside or more, and completely not acting on soluble starch;

(c) optimum pH and stable pH range: optimum pH in about pH 6.0 to 9.0, and stable pH range from pH 5.0 to 10.0 at 25° C. for 20 hours in the presence of 0.2% bovine serum albumin;

(d) suitable temperature range for action: from about 52° C. to about 55° C.;

(e) conditions for inactivation by pH and temperature: stable in the range of pH 5.0 to 10.0, and completely inactivated at pH 4.5 or less or pH 11.0 or more, for 20 hours at 25° C. in the presence of 0.2% bovine serum albumin, and stable at a temperature of up to 50° C. at pH 7.0 for 15 minutes, and completely inactivated at a temperature of 60° C. or more; and (f) molecular weight: about 61,300±5,000 (gel filtration).

2. A process for producing the α-glucosidase according to claim 1, which comprises culturing a strain belonging to the genus Bacillus capable of producing α-glucosidase in a culture and then recovering the α-glucosidase from the culture.

3. The process according to claim 2, wherein the strain belonging to the genus Bacillus is Bacillus sp. KS-108a.

* * * * *